US009464068B2

United States Patent
Echigo

(10) Patent No.: US 9,464,068 B2
(45) Date of Patent: Oct. 11, 2016

(54) ALLYL COMPOUND AND METHOD FOR PRODUCING THE SAME

(71) Applicant: Mitsubishi Gas Chemical Company, Inc., Tokyo (JP)

(72) Inventor: Masatoshi Echigo, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/766,391

(22) PCT Filed: Jan. 24, 2014

(86) PCT No.: PCT/JP2014/051471
§ 371 (c)(1),
(2) Date: Aug. 6, 2015

(87) PCT Pub. No.: WO2014/123005
PCT Pub. Date: Aug. 14, 2014

(65) Prior Publication Data
US 2015/0368224 A1    Dec. 24, 2015

(30) Foreign Application Priority Data

Feb. 8, 2013    (JP) .................................. 2013-023689

(51) Int. Cl.
| | | |
|---|---|---|
| C07D 311/78 | (2006.01) | |
| B01J 27/232 | (2006.01) | |
| C07C 43/215 | (2006.01) | |
| C07C 41/01 | (2006.01) | |

(52) U.S. Cl.
CPC ............. *C07D 311/78* (2013.01); *C07C 41/01* (2013.01); *C07C 43/215* (2013.01); *B01J 27/232* (2013.01)

(58) Field of Classification Search
CPC ............................ C07D 311/78; B01J 27/232
See application file for complete search history.

(56) References Cited

FOREIGN PATENT DOCUMENTS

| JP | 2004-137200 A | 5/2004 |
|---|---|---|
| JP | 2009-51780 A | 3/2009 |
| JP | 2010-6770 A | 1/2010 |
| JP | 2011-225644 A | 11/2011 |
| JP | 2011-236415 A | 11/2011 |
| JP | 2012-68652 A | 4/2012 |
| JP | 2012-93784 A | 5/2012 |
| JP | 2012-118551 A | 6/2012 |
| JP | 2012-131749 A | 7/2012 |
| WO | 2006/132139 A1 | 12/2006 |
| WO | 2011/078060 A1 | 6/2011 |

OTHER PUBLICATIONS

Dayananda, K., et al, Photochemical attachment of polymers on planar surfaces with a covalently anchored monolayer of a novel naphthyl ketone photochemical radical generator, Journal of Polymer Science, Part A: Polymer Chemistry, 42(21), 5413-5423 (2004).*
International Search Report date of mailing Apr. 8, 2014 for PCT/JP2014/051471 and English translation of the same (4 pages).
K. Dayananda et. al., Journal of Polymer Science, Part A, Polymer Chemistry, 2004, 42(21), pp. 5413-5423.
Y. Nakamura et. al., Heterocycles, 1976, 5(1), pp. 427-443.

* cited by examiner

*Primary Examiner* — Erich A Leeser
(74) *Attorney, Agent, or Firm* — Fitch, Even, Tabin & Flannery LLP

(57) ABSTRACT

The allyl compound of the present invention is represented by general formula (α):

$$\left(\diagup\!\!\!\diagdown\!\!\!\diagup O\right)_{m}\!\!\!-\!\!\!\underset{(R)_{n}}{\underset{|}{Z^{1}}}\!\!\!-\!\!\!\underset{X}{\underset{|}{\phantom{Z}}}\!\!\!-\!\!\!\underset{(R)_{n}}{\underset{|}{Z^{2}}}\!\!\!-\!\!\!\left(O\diagdown\!\!\!\diagup\!\!\!\diagdown\right)_{m} \quad (\alpha)$$

wherein ring $Z^1$ is a naphthalene ring, ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

8 Claims, No Drawings

ALLYL COMPOUND AND METHOD FOR PRODUCING THE SAME

CROSS-REFERENCE TO RELATED APPLICATIONS

This application is a U.S. national phase application filed under 35 U.S.C. §371 of International Application PCT/JP2014/051471, filed on Jan. 24, 2014, designating the United States, which claims priority from Japanese Application Number 2013-023689, filed Feb. 8, 2013, which are hereby incorporated herein by reference in their entirety.

TECHNICAL FIELD

The present invention relates to a novel allyl compound and a method for producing the same.

BACKGROUND ART

It is known that allyl compounds having a bisphenol skeleton are useful as components of photoresists, resin raw materials or resin curing agents for electrical and electronic component material and structural material applications (for example, see Japanese Patent Laid-Open Nos. 2004-137200; 2009-51780; 2012-131749; 2012-068652; 2012-093784 and 2012-118551).

SUMMARY OF INVENTION

In recent years, as components of photoresists, resin raw materials or resin curing agents for electrical and electronic component material and structural material applications, further improvement in various properties (optical properties, heat resistance, water resistance, moisture resistance, chemical resistance, electrical properties, mechanical properties, dimensional stability, and the like) has been required, and therefore, the development of a novel allyl compound that meets the requirement has been desired.

Accordingly, an object of the present invention is to provide a novel allyl compound having high heat resistance useful, for example, as a component of a photoresist or a component of a curable resin such as bismaleimide.

The present inventor has studied diligently in order solve the above problem, and as a result found that a novel allyl compound having a particular structure can solve the above problem, arriving at the present invention.

Specifically, the present invention is as follows.

[1]
An allyl compound represented by general formula (α):

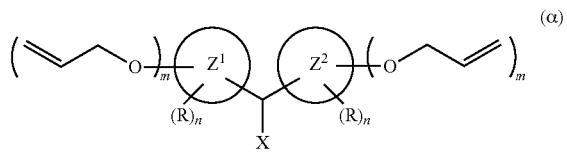

wherein ring $Z^1$ is a naphthalene ring, ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

[2]
A method for producing the allyl compound according to the above [1], comprising a step of reacting a compound represented by the following general formula (β) with an allyl group-introducing reagent in the presence of a base catalyst,

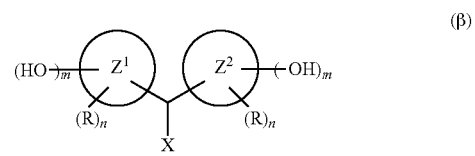

wherein ring $Z^1$ is a naphthalene ring, ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

[3]
The allyl compound according to the above [1], wherein the allyl compound represented by the general formula (α) is an allyl compound represented by the following general formula (1):

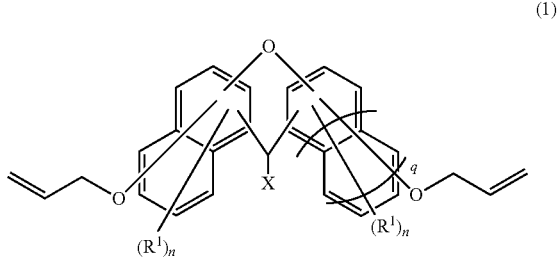

wherein X is a hydrogen atom or a monovalent substituent having 1 to 18 carbon atoms, $R^1$ is each independently an alkyl group having 1 to 4 carbon atoms or a halogen atom, n is each independently an integer of 0 to 5, and q is 0 or 1.

[4]
The allyl compound according to the above [3], wherein the allyl compound represented by the general formula (1) is a compound represented by the following general formula (1-1):

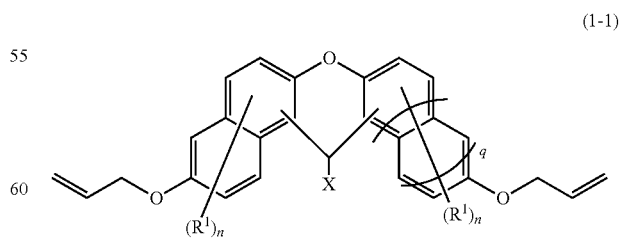

wherein $R^1$, X, n, and q are as in the formula (1).

[5]
A method for producing the allyl compound according to the above [3], comprising a step of reacting a compound represented by the following general formula (2) with an allyl group-introducing reagent in the presence of a base catalyst,

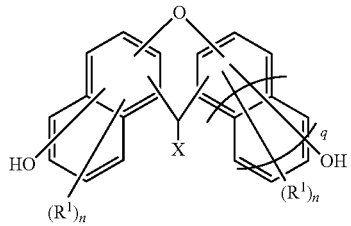

wherein X is a hydrogen atom or a monovalent substituent having 1 to 18 carbon atoms, $R^1$ is each independently an alkyl group having 1 to 4 carbon atoms or a halogen atom, n is each independently an integer of 0 to 5, and q is 0 or 1.

[6]

The allyl compound according to the above [1], wherein the allyl compound represented by the general formula (α) is an allyl compound represented by the following general formula (1'):

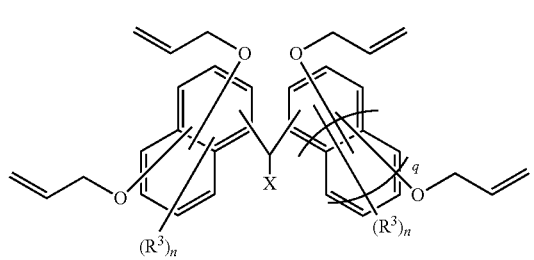

wherein X is a hydrogen atom or a monovalent substituent having 1 to 18 carbon atoms, $R^3$ is each independently an alkyl group having 1 to 4 carbon atoms or a halogen atom, n is each independently an integer of 0 to 5, and q is 0 or 1.

[7]

The allyl compound according to the above [6], wherein the allyl compound represented by the general formula (1') is a compound represented by the following general formula (1'-1):

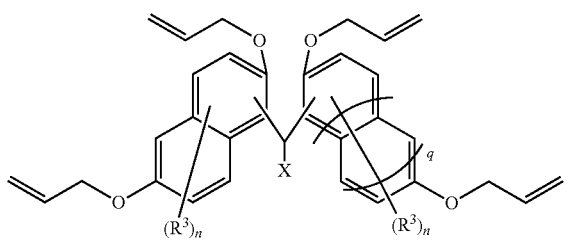

wherein $R^3$, X, n, and q are as in the formula (1').

[8]

A method for producing the allyl compound according to the above [6], comprising a step of reacting a compound represented by the following general formula (2') with an allyl group-introducing reagent in the presence of a base catalyst,

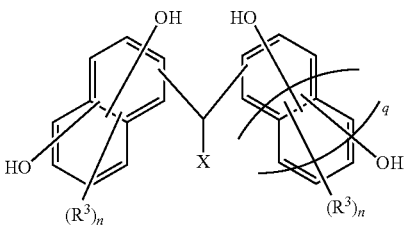

wherein X is a hydrogen atom or a monovalent substituent having 1 to 18 carbon atoms, $R^3$ is each independently an alkyl group having 1 to 4 carbon atoms or a halogen atom, n is each independently an integer of 0 to 5, and q is 0 or 1.

The allyl compound of the present invention has a polycyclic aromatic structure and therefore has excellent heat resistance and is useful as a component of a photoresist or the like or a component of a curable resin such as bismaleimide.

Hereinafter, an embodiment of the present invention (hereinafter, also described as "the present embodiment") will be described in detail. The following embodiment is an illustration for explaining the present invention, and the present invention is not limited to only the embodiment.

An allyl compound of the present embodiment is represented by general formula (α):

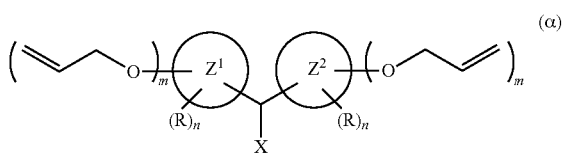

wherein the ring $Z^1$ is a naphthalene ring, the ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

A method for producing the allyl compound of the present embodiment comprises the step of reacting a compound represented by the following general formula (β) with an allyl group-introducing reagent in the presence of a base catalyst.

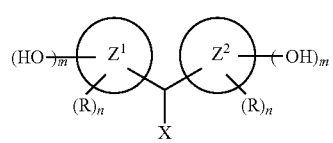

wherein the ring $Z^1$ is a naphthalene ring, the ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

The allyl compound and the method for producing the same of the present embodiment will be described in detail below by taking allyl compounds represented by particular formulas as examples.

The allyl compound of the present embodiment is preferably an allyl compound represented by the following general formula (1):

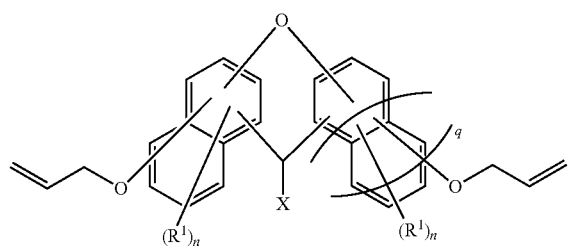

(1)

wherein X is a hydrogen atom or a monovalent substituent having 1 to 18 carbon atoms, $R^1$ is each independently an alkyl group having 1 to 4 carbon atoms or a halogen atom, n is each independently an integer of 0 to 5, and q is 0 or 1.

X in the above general formula (1) is a hydrogen atom or a monovalent substituent having 1 to 18 carbon atoms. The monovalent substituent having 1 to 18 carbon atoms is not particularly limited, and examples thereof include a methyl group, an ethyl group, a propyl group, a butyl group, a pentyl group, a hexyl group, a heptyl group, an octyl group, a nonyl group, a decyl group, an octadecyl group, a cyclopropyl group, a cyclohexyl group, an adamantyl group, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group. Among these, from the viewpoint of heat resistance, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group having an aromatic ring skeleton are preferred, and among them, particularly, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group are more preferred.

In the above general formula (1), $R^1$ is each independently an alkyl group having 1 to 4 carbon atoms or a halogen atom. The alkyl group having 1 to 4 carbon atoms is not particularly limited, and examples thereof include a methyl group, an ethyl group, a propyl group, and a butyl group. The halogen atom is not particularly limited, and examples thereof include a fluorine atom, a chlorine atom, a bromine atom, and an iodine atom.

In terms of heat resistance, in the present embodiment, the allyl compound represented by the above general formula (1) is preferably an allyl compound represented by the following general formula (1-1):

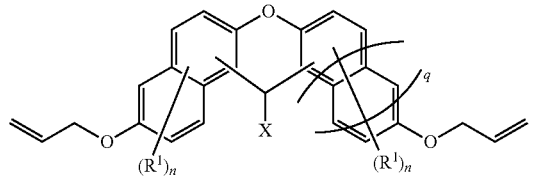

(1-1)

wherein $R^1$, X, n, and q are as in the above formula (1).

Examples of the method for producing the allyl compound represented by the above general formula (1) include a production method comprising the step of reacting a compound represented by the following general formula (2) with an allyl group-introducing reagent in the presence of a base catalyst. The production method preferably comprises the step of obtaining the allyl compound represented by general formula (1) from the reaction liquid obtained in the above step by separation and purification operation such as crystallization. This method is preferred because particularly the amount of by-products is small, and the allyl compound represented by general formula (1) can be efficiently produced.

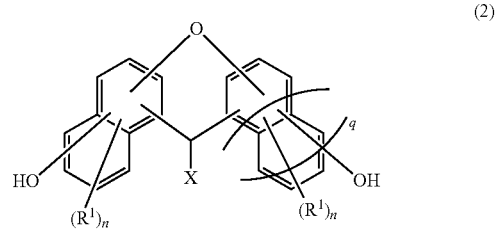

(2)

wherein X is a hydrogen atom or a monovalent substituent having 1 to 18 carbon atoms, $R^1$ is each independently an alkyl group having 1 to 4 carbon atoms or a halogen atom, n is each independently an integer of 0 to 5, and q is 0 or 1.

In terms of heat resistance, in the present embodiment, the compound represented by the above general formula (2) is preferably a compound represented by the following general formula (2-1):

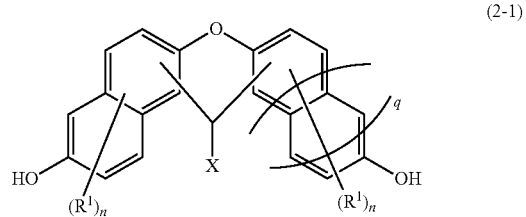

(2-1)

wherein $R^1$, X, n, and q are as in the above formula (2).

As one example of the method for producing an allyl compound of the present embodiment, a method for producing a compound represented by the following formula (4) will be specifically described below. 1 mol of a compound represented by the following formula (3), 2.6 mol of allyl bromide, and 5.2 mol of potassium carbonate are placed in a 3 L flask and reacted in a dimethylformamide solvent at 90° C. while being heated in an oil bath. Then, the reaction solution is cooled to crystallize crude crystals for extraction. The obtained crude crystals and sodium hydroxide are refluxed with a methanol solvent for 4 hours and cooled by air cooling to precipitate crystals. The precipitated crystals are filtered and rinsed, and thus, the compound represented by the following formula (4) can be produced.

(3)

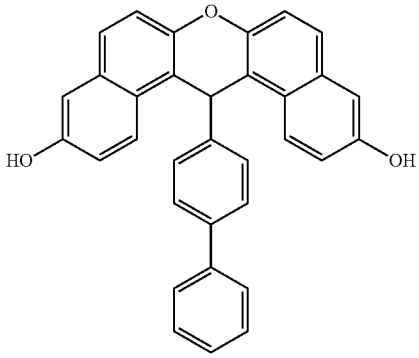

(4)

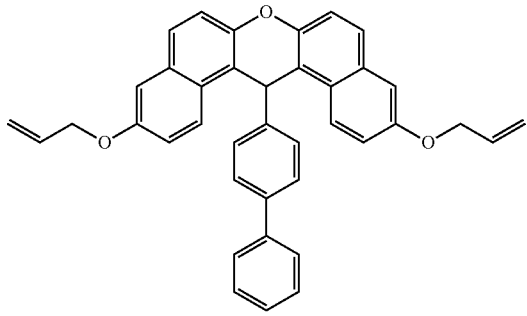

The compound represented by general formula (2) used in the present embodiment can be produced, for example, by reacting a compound represented by the following general formula (5) with an aldehyde having 1 to 19 carbon atoms at relatively high temperature in the presence of an acid catalyst. In the method for producing the compound represented by general formula (2') by reacting a compound represented by the following general formula (5) with an aldehyde having 1 to 19 carbon atoms at a relatively high temperature of 60 to 120° C. in the presence of an acid catalyst, particularly the amount of by-products is small, and the compound represented by general formula (2) can be efficiently produced. In the production method, the structure of the substituent X in the produced compound represented by general formula (2) is determined by what is used as the aldehyde. As a specific illustration, the compound represented by the above formula (3) can be produced by reacting 2,6-naphthalenediol with 4-biphenylcarboxaldehyde in the presence of a sulfuric acid catalyst at 100° C.

(5)

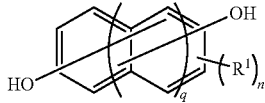

wherein $R^1$ is an alkyl group having 1 to 4 carbon atoms or a halogen atom, n is an integer of 0 to 5, and q is 0 or 1.

The compound represented by general formula (5) is preferably a compound having a dihydroxynaphthalene skeleton. It can be expected that the performance of an allyl compound derived using a compound having a dihydroxynaphthalene skeleton is more improved in heat resistance than that of an allyl compound derived using only a dihydroxy compound having a benzene ring skeleton. The compound having a dihydroxynaphthalene skeleton is not particularly limited, and examples thereof include naphthalenediol, methylnaphthalenediol, ethylnaphthalenediol, propylnaphthalenediol, butylnaphthalenediol, fluoronaphthalenediol, chloronaphthalenediol, bromonaphthalenediol, and iodonaphthalenediol. These are easily available as reagents.

In addition, as the compound having a dihydroxynaphthalene skeleton, one type or two or more types can be used.

Further, the above compound having a dihydroxynaphthalene skeleton and a dihydroxy compound having a benzene ring skeleton can also be used in combination. The dihydroxy compound having a benzene ring skeleton used in combination is not particularly limited, and examples thereof include benzenediol, methylbenzenediol, ethylbenzenediol, propylbenzenediol, butylbenzenediol, fluorobenzenediol, chlorobenzenediol, bromobenzenediol, and iodobenzenediol.

By using the above compound having a dihydroxynaphthalene skeleton and a dihydroxy compound having a benzene ring skeleton in combination, a compound in which one is a naphthalene skeleton and the other is a benzene skeleton can be derived in the finally obtained compound represented by the above formula (1).

The above aldehyde having 1 to 19 carbon atoms is not particularly limited, and examples thereof include formaldehyde, acetaldehyde, propionaldehyde, butyraldehyde, pentyl aldehyde, hexyl aldehyde, heptyl aldehyde, octyl aldehyde, nonyl aldehyde, decyl aldehyde, octadecyl aldehyde, cyclopropyl aldehyde, cyclohexyl aldehyde, adamantylcarboxaldehyde, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxaldehyde, terphenylcarboxaldehyde, naphthalenecarboxaldehyde, anthracenecarboxaldehyde, phenanthrenecarboxaldehyde, and pyrenecarboxaldehyde. Among these, from the viewpoint of heat resistance, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxaldehyde, terphenylcarboxaldehyde, naphthalenecarboxaldehyde, anthracenecarboxaldehyde, phenanthrenecarboxaldehyde, and pyrenecarboxaldehyde having an aromatic ring are preferred, and among them, particularly, biphenylcarboxaldehyde, terphenylcarboxaldehyde, naphthalenecarboxaldehyde, anthracenecarboxaldehyde, phenanthrenecarboxaldehyde, and pyrenecarboxaldehyde are more preferred.

The aldehyde having 1 to 19 carbon atoms is easily available as an industrial product or a reagent.

In addition, as the aldehyde having 1 to 19 carbon atoms, one type or two or more types can be used.

The allyl group-introducing reagent used in the present embodiment is not particularly limited as long as an allyl group represented by the following formula (6) can be introduced into a hydroxyl group of the compound represented by general formula (2) (the hydrogen atom of a hydroxyl group of the compound represented by general formula (2) can be replaced by an allyl group). Examples of the allyl group-introducing reagent include allyl chloride, allyl bromide, and allyl iodide.

In addition, as the allyl group-introducing reagent, one type or two or more types can be used.

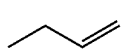

(6)

In the production method of the present embodiment, the base catalyst used for the reaction of the compound represented by general formula (2) with the allyl group-introducing reagent can be appropriately selected from well-known base catalysts and is not particularly limited. Examples of the base catalyst include inorganic bases such as metal hydroxides (alkali metal or alkaline-earth metal hydroxides such as sodium hydroxide and potassium hydroxide, and the like), metal carbonates (alkali metal or alkaline-earth metal carbonates such as sodium carbonate and potassium carbonate, and the like), and alkali metal or alkaline-earth metal hydrogen carbonates such as sodium hydrogen carbonate and potassium hydrogen carbonate, and organic bases such as amines (for example, tertiary amines (trialkylamines such as triethylamine, aromatic tertiary amines such as N,N-dimethylaniline, and heterocyclic tertiary amines such as 1-methylimidazole) and metal carboxylates (alkali metal or alkaline-earth metal acetates such as sodium acetate and calcium acetate, and the like). From production viewpoints such as availability and ease of handling, sodium carbonate and potassium carbonate are preferred.

In addition, as the base catalyst, one type or two or more types can be used.

Next, the conditions of the reaction of the compound represented by general formula (2) with the allyl group-introducing reagent will be described in detail.

The reaction is preferably performed using, for example, 1 mol to an excess amount of the allyl group-introducing reagent and 0.001 to 1 mol of the base catalyst based on 1 mol of the compound represented by general formula (2). In addition, the reaction pressure is preferably normal pressure, the reaction temperature is preferably 20 to 150° C., and the reaction time is preferably 20 minutes to 100 hours. After the reaction, the target material can be purified by a known method. The purification method is not particularly limited, and examples thereof include a method of performing cooling with ice water or the like to precipitate crystals followed by isolation to obtain crude crystals.

Then, it is preferred that the crude crystals are dissolved in an organic solvent, a strong base is added to the obtained solution, and the mixture is reacted, for example, at normal pressure at 20 to 150° C. for about 20 minutes to 100 hours. After the reaction, the target material can be isolated by a known method. The isolation method is not particularly limited, and examples thereof include the following method. First, the above reaction liquid is concentrated, and pure water is added to precipitate the reaction products. The reaction liquid in which the reaction products are precipitated is cooled to room temperature and then filtered to separate the solids. The obtained solids are dried followed by purification by separation from the by-products by column chromatography, the distilling off of the solvent, filtration, and drying, and the target compound represented by general formula (1) can be obtained.

The allyl compound of the present embodiment is preferably an allyl compound represented by the following general formula (1').

The allyl compound represented by the following general formula (1') will be described in detail below.

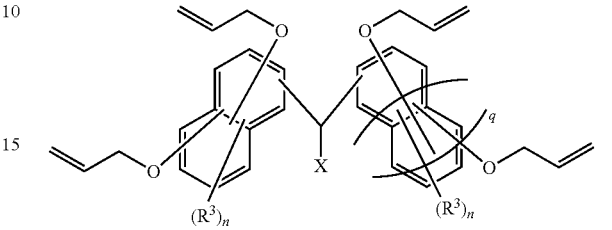

(1')

wherein X is a hydrogen atom or a monovalent substituent having 1 to 18 carbon atoms, $R^3$ is each independently an alkyl group having 1 to 4 carbon atoms or a halogen atom, n is each independently an integer of 0 to 5, and q is 0 or 1.

X in the above general formula (1') is a hydrogen atom or a monovalent substituent having 1 to 18 carbon atoms. The monovalent substituent having 1 to 18 carbon atoms is not particularly limited, and examples thereof include a methyl group, an ethyl group, a propyl group, a butyl group, a pentyl group, a hexyl group, a heptyl group, an octyl group, a nonyl group, a decyl group, an octadecyl group, a cyclopropyl group, a cyclohexyl group, an adamantyl group, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group. Among these, from the viewpoint of heat resistance, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group having an aromatic ring skeleton are preferred, and among them, particularly, a phenyl group, a tosyl group, a dimethylphenyl group, an ethylphenyl group, a propylphenyl group, a butylphenyl group, a cyclohexylphenyl group, a biphenyl group, a terphenyl group, a naphthyl group, an anthracyl group, a phenanthryl group, and a pyrenyl group are more preferred.

In the above general formula (1'), $R^3$ is each independently an alkyl group having 1 to 4 carbon atoms or a halogen atom. The alkyl group having 1 to 4 carbon atoms is not particularly limited, and examples thereof include a methyl group, an ethyl group, a propyl group, and a butyl group. The halogen atom is not particularly limited, and examples thereof include a fluorine atom, a chlorine atom, a bromine atom, and an iodine atom.

In terms of heat resistance, in the present embodiment, the allyl compound represented by the above general formula (1') is preferably an allyl compound represented by the following general formula (1'-1):

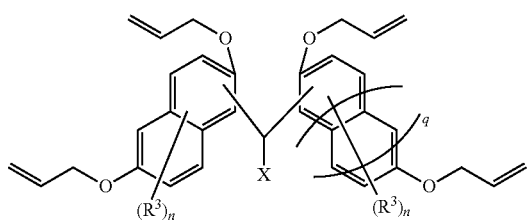

(1'-1)

wherein R³, X, n, and q are as in the above formula (1').

Examples of the method for producing the allyl compound represented by the above general formula (1') include a production method comprising the step of reacting a compound represented by the following general formula (2') with an allyl group-introducing reagent in the presence of a base catalyst. The production method preferably comprises the step of obtaining the allyl compound represented by general formula (1') from the reaction liquid obtained in the above step by separation and purification operation such as crystallization. This method is preferred because particularly the amount of by-products is small, and the allyl compound represented by general formula (1') can be efficiently produced.

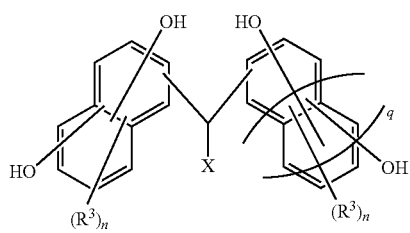

(2')

wherein X is a hydrogen atom or a monovalent substituent having 1 to 18 carbon atoms, R³ is each independently an alkyl group having 1 to 4 carbon atoms or a halogen atom, n is each independently an integer of 0 to 5, and q is 0 or 1.

In terms of heat resistance, in the present embodiment, the compound represented by the above general formula (2') is preferably a compound represented by the following general formula (2'-1):

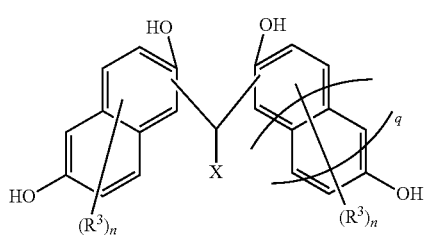

(2'-1)

wherein R³, X, n, and q are as in the above formula (2').

As one example of the method for producing an allyl compound of the present embodiment, a method for producing a compound represented by the following formula (4') will be specifically described below. 1 mol of a compound represented by the following formula (3'), 5.2 mol of allyl bromide, and 10.4 mol of potassium carbonate are placed in a 3 L flask and reacted in a dimethylformamide solvent at 90° C. while being heated in an oil bath. Then, the reaction solution is cooled to crystallize crude crystals for extraction. The obtained crude crystals and sodium hydroxide are refluxed with a methanol solvent for 4 hours and cooled by air cooling to precipitate crystals. The precipitated crystals are filtered and rinsed, and thus, the compound represented by the following formula (4') can be produced.

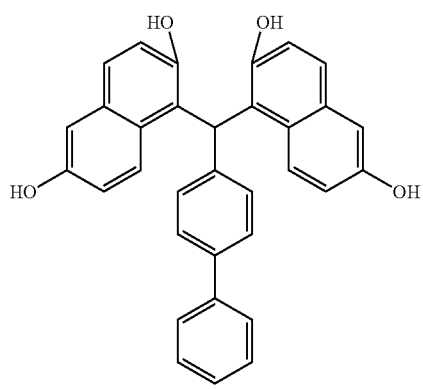

(3')

(4')

The compound represented by general formula (2') used in the present embodiment can be produced, for example, by reacting a compound represented by the following general formula (5') with an aldehyde having 1 to 19 carbon atoms at a relatively low temperature of 20 to 60° C. in the presence of an acid catalyst. In the method for producing the compound represented by general formula (2') by reacting a compound represented by the following formula (5') with an aldehyde having 1 to 19 carbon atoms at relatively low temperature in the presence of an acid catalyst, particularly the amount of by-products is small, and the compound represented by general formula (2') can be efficiently produced. In the production method, the structure of the substituent X in the produced compound represented by general formula (2') is determined by what is used as the aldehyde. As a specific illustration, the compound represented by the above formula (3') can be produced by reacting 2,6-naphthalenediol with 4-biphenylcarboxaldehyde in the presence of a sulfuric acid catalyst at 30° C.

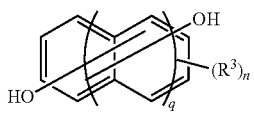

(5')

wherein $R^3$ is an alkyl group having 1 to 4 carbon atoms or a halogen atom, n is an integer of 0 to 5, and q is 0 or 1.

The compound represented by general formula (5') used in the present embodiment is preferably a compound having a dihydroxynaphthalene skeleton. It can be expected that the performance of an allyl compound derived using a compound having a dihydroxynaphthalene skeleton is more improved in heat resistance than that of an allyl compound derived using only a dihydroxy compound having a benzene ring skeleton. The compound having a dihydroxynaphthalene skeleton is not particularly limited, and examples thereof include naphthalenediol, methylnaphthalenediol, ethylnaphthalenediol, propylnaphthalenediol, butylnaphthalenediol, fluoronaphthalenediol, chloronaphthalenediol, bromonaphthalenediol, and iodonaphthalenediol. These are easily available as reagents.

In addition, as the compound having a dihydroxynaphthalene skeleton, one type or two or more types can be used.

Further, the above compound having a dihydroxynaphthalene skeleton and a dihydroxy compound having a benzene ring skeleton can also be used in combination. The dihydroxy compound having a benzene ring skeleton used in combination is not particularly limited, and, for example, benzenediol, methylbenzenediol, ethylbenzenediol, propylbenzenediol, butylbenzenediol, fluorobenzenediol, chlorobenzenediol, bromobenzenediol, and iodobenzenediol are used.

By using the above compound having a dihydroxynaphthalene skeleton and a dihydroxy compound having a benzene ring skeleton in combination, a compound in which one is a naphthalene skeleton and the other is a benzene skeleton can be derived in the finally obtained compound represented by the above formula (1').

In the production method of the present embodiment, the structure of the substituent X in the produced compound represented by general formula (2') is determined by what is used as the aldehyde having 1 to 19 carbon atoms. The aldehyde is not particularly limited, and examples thereof include formaldehyde, acetaldehyde, propionaldehyde, butyraldehyde, pentyl aldehyde, hexyl aldehyde, heptyl aldehyde, octyl aldehyde, nonyl aldehyde, decyl aldehyde, octadecyl aldehyde, cyclopropyl aldehyde, cyclohexyl aldehyde, adamantylcarboxaldehyde, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxaldehyde, terphenylcarboxaldehyde, naphthalenecarboxaldehyde, anthracenecarboxaldehyde, phenanthrenecarboxaldehyde, and pyrenecarboxaldehyde. Among these, from the viewpoint of heat resistance, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxaldehyde, terphenylcarboxaldehyde, naphthalenecarboxaldehyde, anthracenecarboxaldehyde, phenanthrenecarboxaldehyde, and pyrenecarboxaldehyde having an aromatic ring are preferred, and among them, particularly, biphenylcarboxaldehyde, terphenylcarboxaldehyde, naphthalenecarboxaldehyde, anthracenecarboxaldehyde, phenanthrenecarboxaldehyde, and pyrenecarboxaldehyde are more preferred.

The aldehyde having 1 to 19 carbon atoms is easily available as an industrial product or a reagent.

In addition, as the aldehyde having 1 to 19 carbon atoms, one type or two or more types can be used.

The allyl group-introducing reagent used in the present embodiment is not particularly limited as long as an allyl group represented by general formula (6') can be introduced into a hydroxyl group of the compound represented by the above general formula (2') (the hydrogen atom of a hydroxyl group of the compound represented by general formula (2') can be replaced by an allyl group). Examples of the allyl group-introducing reagent include allyl chloride, allyl bromide, and allyl iodide.

In addition, as the allyl group-introducing reagent, one type or two or more types can be used.

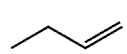

(6')

In the production method of the present embodiment, the base catalyst used for the reaction of the compound represented by general formula (2') with the allyl group-introducing reagent can be appropriately selected from well-known base catalysts and is not particularly limited. Examples of the base catalyst include inorganic bases such as metal hydroxides (alkali metal or alkaline-earth metal hydroxides such as sodium hydroxide and potassium hydroxide, and the like), metal carbonates (alkali metal or alkaline-earth metal carbonates such as sodium carbonate and potassium carbonate, and the like), and alkali metal or alkaline-earth metal hydrogen carbonates such as sodium hydrogen carbonate and potassium hydrogen carbonate, and organic bases such as amines (for example, tertiary amines (trialkylamines such as triethylamine, aromatic tertiary amines such as N,N-dimethylaniline, and heterocyclic tertiary amines such as 1-methylimidazole) and metal carboxylates (alkali metal or alkaline-earth metal acetates such as sodium acetate and calcium acetate, and the like). From production viewpoints such as availability and ease of handling, sodium carbonate and potassium carbonate are preferred.

In addition, as the base catalyst, one type or two or more types can be used.

Next, the conditions of the reaction of the compound represented by general formula (2') with the allyl group-introducing reagent will be described in detail.

The reaction is preferably performed using, for example, 1 mol to an excess amount of the allyl group-introducing reagent and 0.001 to 1 mol of the base catalyst based on 1 mol of the compound represented by general formula (2'). In addition, the reaction pressure is preferably normal pressure, the reaction temperature is preferably 20 to 150° C., and the reaction time is preferably 20 minutes to 100 hours. After the reaction, the target material can be purified by a known method. The purification method is not particularly limited, and examples thereof include a method of performing cooling with ice water or the like to precipitate crystals followed by isolation to obtain crude crystals.

Then, it is preferred that the crude crystals are dissolved in an organic solvent, a strong base is added to the obtained solution, and the mixture is reacted, for example, at normal pressure at 20 to 150° C. for about 20 minutes to 100 hours.

After the reaction, the target material can be isolated by a known method. The isolation method is not particularly limited, and examples thereof include the following method. First, the above reaction liquid is concentrated, and pure water is added to precipitate the reaction products. The reaction liquid in which the reaction products are precipitated is cooled to room temperature and then filtered to separate the solids. The obtained solids are filtered and dried followed by purification by separation from the by-products by column chromatography, the distilling off of the solvent, filtration, and drying, and the target compound represented by general formula (1') can be obtained.

EXAMPLES

The embodiment of the present invention will be more specifically described below by giving Examples. However, the present invention is not particularly limited to these Examples.

The method for evaluating a compound is as follows.

<Measurement of Pyrolysis Temperature>

Using an EXSTAR6000DSC apparatus manufactured by SII NanoTechnology Inc., the pyrolysis temperature of a compound was measured as follows. About 5 mg of a sample was placed in an unsealed container made of aluminum, and the container was set in the above apparatus. The temperature was increased to 500° C. at a temperature increase rate of 10° C./min in a nitrogen gas (30 mL/min) gas flow. At this time, the temperature at which a decrease portion appeared in the base line was taken as the pyrolysis temperature.

Synthesis Example 1

A container having an internal volume of 100 mL equipped with a stirrer, a cooling tube, and a buret was charged with a solution obtained by dissolving 3.20 g (20 mmol) of 2,6-naphthalenediol (reagent manufactured by Sigma-Aldrich Corporation) and 1.82 g (10 mmol) of 4-biphenylcarboxaldehyde (manufactured by Mitsubishi Gas Chemical Company, Inc.) in 30 ml of methyl isobutyl ketone, and 5 ml of 95% sulfuric acid was further added. The obtained reaction liquid was stirred at 100° C. for 6 hours for reaction. Next, the reaction liquid was concentrated, and 50 g of pure water was added to precipitate the reaction products. The reaction liquid was cooled to room temperature. Then, the reaction liquid was filtered to separate the reaction liquid into a filtrate and solids. The obtained solids were dried and then subjected to separation and purification by column chromatography, and 3.05 g of a compound represented by the following formula (3) was obtained. The fact that the obtained compound had the chemical structure of the following formula (3) was confirmed by 400 MHz $^1$H-NMR as follows.

$^1$H-NMR: (d-DMSO, internal standard TMS)

δ (ppm) 9.7 (2H, O—H), 7.2-8.5 (19H, Ph-H), 6.6 (1H, C—H)

The fact that the substitution position of 2,6-naphthalenediol was position 1 was confirmed from the fact that the signals of the protons at positions 3 and 4 were doublets.

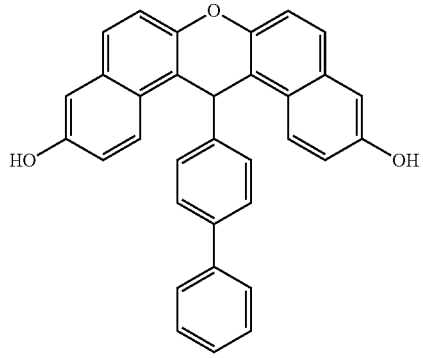

(3)

Example 1

A container having an internal volume of 200 mL equipped with a stirrer, a cooling tube, and a buret was charged with a solution obtained by dissolving 5.8 g (12.4 mmol) of the compound represented by formula (3) obtained above and 4 g (28 mmol) of potassium carbonate in 100 mL of acetone, and 3.3 g (27 mmol) of allyl bromide and 0.8 g of 10-crown-6 were further added. The obtained reaction liquid was stirred under reflux for 7 hours for reaction. Next, the reaction liquid was cooled in an ice bath, and the reaction liquid was concentrated to precipitate solids. The precipitated solids were filtered, dried, and then subjected to separation and purification by column chromatography, and 2.0 g of a target compound represented by the following formula (4) was obtained. The fact that the obtained compound had the chemical structure of the following formula (4) was confirmed by 400 MHz $^1$H-NMR as follows.

$^1$H-NMR: (d-DMSO, internal standard TMS)

δ (ppm) 7.2-7.8 (19H, Ph-H), 6.7 (1H, C—H), 6.1 (2H, —CH═CH$_2$), 5.4-5.5 (4H, —CH═CH$_2$), 4.7 (4H, —O—CH$_2$—)

It was confirmed that the obtained compound had a pyrolysis temperature of 380° C. and had high heat resistance.

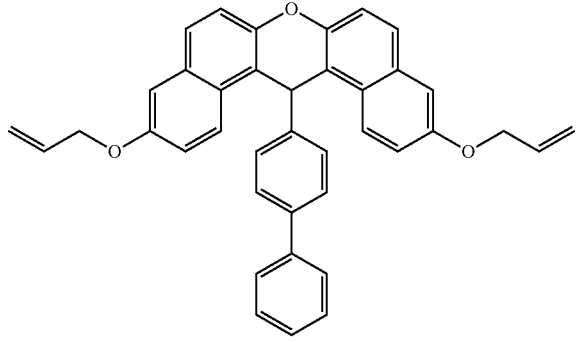

(4)

Synthesis Example 2

A container having an internal volume of 100 mL equipped with a stirrer, a cooling tube, and a buret was charged with a solution obtained by dissolving 3.20 g (20 mmol) of 2,6-naphthalenediol (reagent manufactured by Sigma-Aldrich Corporation) and 1.82 g (10 mmol) of 4-biphenylcarboxaldehyde (manufactured by Mitsubishi Gas Chemical Company, Inc.) in 30 ml of methyl isobutyl ketone, and 5 ml of 95% sulfuric acid was further added. The obtained reaction liquid was stirred at 30° C. for 6 hours for reaction. Next, the reaction liquid was concentrated, and 50 g of pure water was added to precipitate the reaction products. The reaction liquid was cooled to room temperature. Then, the reaction liquid was filtered to separate the reaction liquid into a filtrate and solids. The obtained solids were dried and then subjected to separation and purification by column chromatography, and 0.2 g of a target compound represented by the following formula (3') was obtained. The fact that the obtained compound had the chemical structure of the following formula (3') was confirmed by 400 MHz $^1$H-NMR as follows.

$^1$H-NMR: (d-DMSO, internal standard TMS)

δ (ppm) 9.3-9.4 (4H, O—H), 7.0-8.1 (19H, Ph-H), 6.8 (1H, C—H)

The fact that the substitution position of 2,6-naphthalenediol was position 1 was confirmed from the fact that the signals of the protons at positions 3 and 4 were doublets.

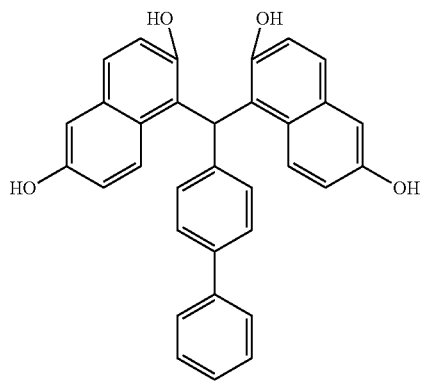

(3')

Example 2

A container having an internal volume of 200 mL equipped with a stirrer, a cooling tube, and a buret was charged with a solution obtained by dissolving 2.9 g (6.2 mmol) of the compound represented by formula (3') obtained above and 4 g (28 mmol) of potassium carbonate in 100 mL of acetone, and 3.3 g (27 mmol) of allyl bromide and 0.8 g of 10-crown-6 were further added. The obtained reaction liquid was stirred under reflux for 7 hours for reaction. Next, the reaction liquid was cooled in an ice bath, and the reaction liquid was concentrated to precipitate solids. The precipitated solids were filtered, dried, and then subjected to separation and purification by column chromatography, and 0.5 g of a target compound represented by the following formula (4') was obtained. The fact that the obtained compound had the chemical structure of the following formula (4') was confirmed by 400 MHz $^1$H-NMR as follows.

$^1$H-NMR: (d-DMSO, internal standard TMS)

δ (ppm): 7.0-8.0 (19H, Ph-H), 6.8 (1H, C—H), 6.1 (4H, —CH═CH$_2$), 5.4-5.5 (8H, —CH═CH$_2$), 4.7 (8H, —O—CH$_2$—)

It was confirmed that the obtained compound had a pyrolysis temperature of 240° C. and had high heat resistance.

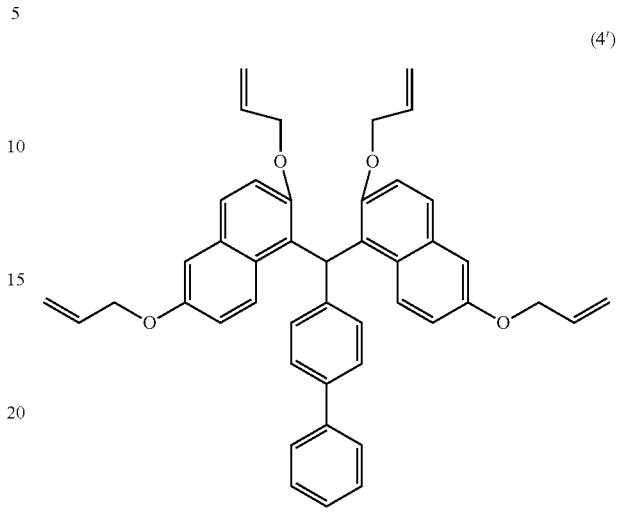

(4')

The invention claimed is:

1. An allyl compound represented by general formula (α):

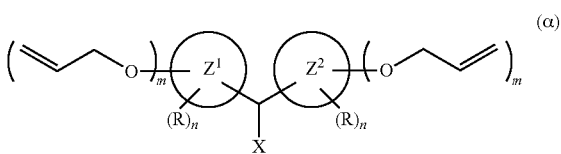

(α)

wherein ring $Z^1$ is a naphthalene ring, ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

2. A method for producing the allyl compound according to claim 1, comprising a step of reacting a compound represented by the following general formula (β) with an allyl group-introducing reagent in the presence of a base catalyst,

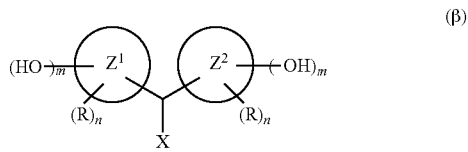

(β)

wherein ring $Z^1$ is a naphthalene ring, ring $Z^2$ is a benzene ring or a naphthalene ring, X is a hydrogen atom or a monovalent substituent having 1 to 18 carbon atoms, R is each independently an alkyl group having 1 to 4 carbon atoms or a halogen atom, m is 1 or 2, n is each independently an integer of 0 to 5, and when m is 1, the ring $Z^1$ and the ring $Z^2$ are bonded to each other via an oxygen atom.

3. An allyl compound represented by general formula (1):

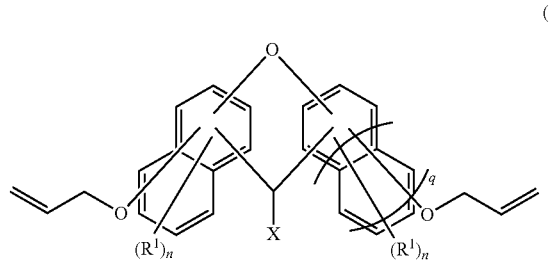
(1)

wherein X is a hydrogen atom or a monovalent substituent having 1 to 18 carbon atoms, $R^1$ is each independently an alkyl group having 1 to 4 carbon atoms or a halogen atom, n is each independently an integer of 0 to 5, and q is 0 or 1.

4. The allyl compound according to claim 3, wherein the allyl compound represented by the general formula (1) is a compound represented by the following general formula (1-1):

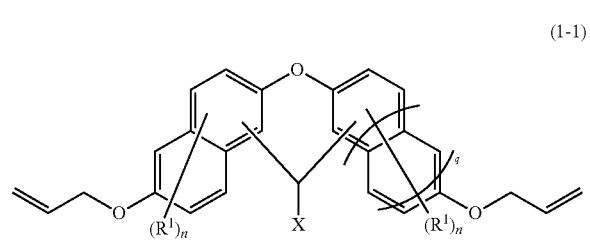
(1-1)

wherein $R^1$, X, n, and q are as in the formula (1).

5. A method for producing the allyl compound according to claim 3, comprising a step of reacting a compound represented by the following general formula (2) with an allyl group-introducing reagent in the presence of a base catalyst,

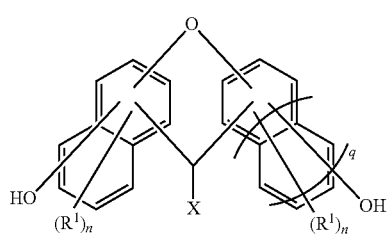
(2)

wherein X is a hydrogen atom or a monovalent substituent having 1 to 18 carbon atoms, $R^1$ is each independently an alkyl group having 1 to 4 carbon atoms or a halogen atom, n is each independently an integer of 0 to 5, and q is 0 or 1.

6. The allyl compound according to claim 1, wherein the allyl compound represented by the general formula (α) is an allyl compound represented by the following general formula (1'):

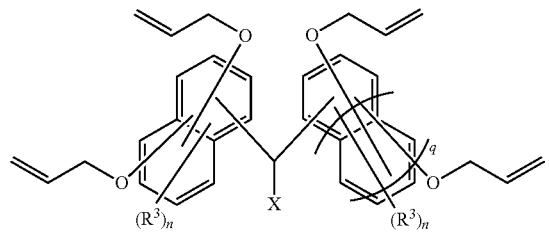
(1')

wherein X is a hydrogen atom or a monovalent substituent having 1 to 18 carbon atoms, $R^3$ is each independently an alkyl group having 1 to 4 carbon atoms or a halogen atom, n is each independently an integer of 0 to 5, and q is 0 or 1.

7. The allyl compound according to claim 6, wherein the allyl compound represented by the general formula (1') is a compound represented by the following general formula (1'-1):

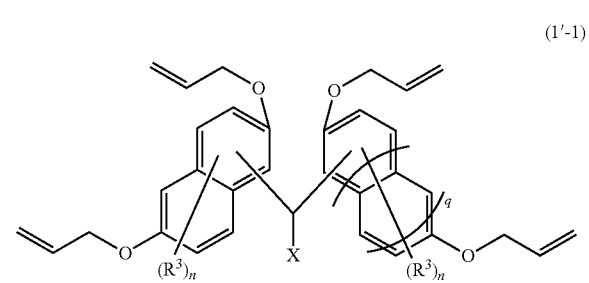
(1'-1)

wherein $R^3$, X, n, and q are as in the formula (1').

8. A method for producing the allyl compound according to claim 6, comprising a step of reacting a compound represented by the following general formula (2') with an allyl group-introducing reagent in the presence of a base catalyst,

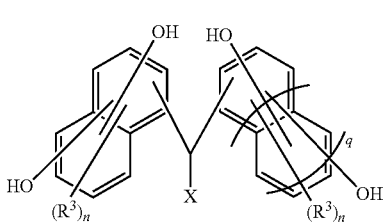
(2')

wherein X is a hydrogen atom or a monovalent substituent having 1 to 18 carbon atoms, $R^3$ is each independently an alkyl group having 1 to 4 carbon atoms or a halogen atom, n is each independently an integer of 0 to 5, and q is 0 or 1.

* * * * *